United States Patent [19]
Chou

[11] Patent Number: 6,117,852
[45] Date of Patent: Sep. 12, 2000

[54] BORON-CONTAINING LIPIODOL FOR BORON NEUTRON CAPTURE THERAPY OF HEPATOMA

[75] Inventor: Fong-In Chou, Hsinchu, Taiwan

[73] Assignee: National Science Council, Taiwan

[21] Appl. No.: 08/999,222

[22] Filed: Dec. 29, 1997

[51] Int. Cl.[7] .......................... A61K 51/12; A61K 9/127; C07F 5/02

[52] U.S. Cl. .......................... 514/64; 424/1.11; 424/1.21; 424/450; 564/8

[58] Field of Search ....................... 514/44, 64; 424/1.21, 424/1.11, 450; 564/4, 8; 565/5

[56] References Cited

U.S. PATENT DOCUMENTS

| | | | |
|---|---|---|---|
| 4,578,391 | 3/1986 | Kawata | 514/256 |
| 5,648,532 | 7/1997 | Hawthorne et al. | 564/8 |

OTHER PUBLICATIONS (2) Hawthorne et al. Preparation of Tumor–Specific Boron Compounds. 1. In Vitro Studies Using Boron–labeled antibodies and Elemental Boron as Neutron Targets. Journal of Medicinal Chemistry vol. 15, No. 5, pp. 449–452, May 1972.

F. I. Chou et al., Lipiodol Uptake and Retention by Human Hepatoma Cells, Nucl. Med. Biol., pp. 379–386, 1995.

F. I. Chou et al., Encapsulation of boron in lipiodol for boron neutron cpature therapy of hepatoma, Advances in Neutron Capture Therapy vol. II, Chemistry and Biology, Elsevier Science, 1997.

Chou et al, "Lipiodol Uptake and Retention by Human Hepatoma Cell", Nucl.Med.Biol. 22(3):379–386, 1995.

*Primary Examiner*—George C. Elliott
*Assistant Examiner*—Janet Epps
*Attorney, Agent, or Firm*—Fish & Richardson P.C.

[57] ABSTRACT

The present invention discloses a boron-containing pharmaceutical composition useful in boron neutron capture therapy of hepatoma, which includes lipiodol, stibmicron boron powder, lecithin and unsaturated fatty acid. The lipiodol has a property of a high retention in hepatoma, the lecithin has a boron carrying capacity, and the unsaturated fatty acid has a function of rendering lecithin soluble in lipiodol.

29 Claims, 2 Drawing Sheets

BORON-CONTAINING LIPIODOL FOR BORON NEUTRON CAPTURE THERAPY OF HEPATOMA

FIELD OF THE INVENTION

The present invention is related to boron neutron capture therapy (BNCT) of hepatoma, and in particular to a lipiodol-based pharmaceutical composition for use in BNCT of hepatoma.

BACKGROUND OF THE INVENTION

Hepatoma is the most common cancer in males and the third most common cancer in females in Taiwan; it is a malignant tumor that responds poorly to current therapies may be candidate for boron neutron capture therapy (BNCT). BNCT is based a nuclear reaction occurring when boron-10 is irradiated with and absorbs thermal, epitlhermal neutrons. A situation in which an atom of boron-10 captures a neutron, causes an unstable isotope, boron-11, to form. The boron-11 instantly decomposes, yielding lithiumLi-7 nuclei and energetic alpha particles. Alpha particles have a pathilcngtli of about one cell diameter and give rise to closely spaced ionizing radiation. Thus, these heavy particles are a highly lethal form of radiation; a few alpha particles releasing their energy within a cancer cell are necessary to destroy it. Above characteristics make BNCT highly destroying cancer cells.

Several recent developments have markedly enhanced the potential of BNCT. If the treatment proceeds as intended, the capture reaction's destructive effects occur primarily in cancer cells having accumulated boron-10. Normal cells with low boron concentrations are spared. Investigators are exploring potential boron carriers such as drugs, monoclonal antibodies and derivatives of naturally occurring compounds. Lipiodol has important therapeutic potential as a carrier vehicle for targeting anti-cancer drugs or radioisotopes for cancer treatment. Encouraging results has been reported in some studies [Kanematsu T. Matsumliata T, Furulta T, Shirabe K, Yamagata M, Utsunomiya T, Sugimachi K. Lipiodol drug targeting in the treatment of primary hepatocellular-carcinonma. Hepato-Gastroenterology (1990) 37:442–444; Lui W Y, Liu R S, Chiang J H, Lo J C, Lai K H, King K L, Cheng H C, Wei Y Y, Chi C W, Peng F K, Chan W K. Report of a pilot study of intra-arterial injection of I-131 lipiodol for the treatment of hepatoma. Chin Med J (Taipei) (1991) 46:125–133]. Moreover, the present inventor and her co-workers in their previously study clearly demonstrated that hepatoma cells in culture are capable of rapidly active uptake of a large quantity of lipiodol by endocytosis with prolonged retention of the lipiodol intracellularly as long as the life span of the cells [Chou F I, Fang K C, Chung C, Lui W Y, Chi C W, Liu R S Chan W K. Lipiodol uptake and retention by human hepatoma cells. Nucl Med Biol (1995) 22(3):379–386]. These findings have major clinical implications for developing new treatment methods for hepatoma patients. To reduce the general toxicity in normal cells in BNCT, in this invention, the present inventor employed lipiodol vesicles as a drug carrier capable of achieving boron drug transport of cancer.

SUMMARY OF THE INVENTION

The present invention discloses a boron-containing lipiodol (B-lipiodol) pharmaceutical composition comprising lipiodol, submicron boron powder, lecithin and $C_{12}$–$C_{22}$ fatty acid, wherein said submicron boron powder is suspended in said lipiodol in the presence of said lecithin and said $C_{12}$–$C_{22}$ fatty acid. This B-lipiodol pharmaceutical composition is at least useful in boron neutron capture therapy (BNCT) of hepatoma. In the B-lipiodol of the present invention, the lipiodol has a property of a high retention in hepatoma, the lecithin has a boron carrying capacity, and the $C_{12}$–$C_{22}$ fatty acid has a function of rendering lecithin soluble in lipiodol.

The present invention also discloses a method for treating hepatoma in a patient comprising administrating a therapeutically effective amount of the B-lipiodol pharmaceutical composition to said patient, and subjecting hepatoma with neutron irradiation.

Preferably, the B-lipiodol of the present invention comprises 0.01–0.3 g lecithin, and 0.01–0.4 g $C_{12}$–$C_{22}$ fatty acid per mL of lipiodol, and 100–5000 ppm submicron boron powder based on the total weight of the B-lipiodol.

Any prior art lipiodol can be used in the present invention as long as it can accumulate in hepatoma cells, for examples, the lipiodol used as X-ray contrast medium and the lipiodol used as lymphography contrast medium. A typical lipiodol is described in the Merck Index, $9^{th}$ edition, page, 4892, which is an iodine addition product of vegetable oils containing 38–42 wt % organically combined iodine.

A suitable lecithin for use in the present invention includes the lecithin obtained from living organisms and the synthetic lecithin. Details of lecithin can be found in the Merck Index, $9^{th}$ edition, pp. 5287–5288, the related disclosure thereof is incorporated by reference. The amount of submicon boron powder which is able to be retained in the B-lipiodol increases as the amount of lecithin contained therein increases, which in turn requires a higher quantity of the $C_{12}$–$C_{22}$ fatty acid to be added to the B-lipiodol in order to render all lecithin soluble in the lipiodol. Preferably, the B-lipiodol contains 0.05–0.2 g lecithin, and more preferably, about 0.15 g lecithin, per mL lipiodol.

A $C_{12}$–$C_{22}$ fatty acid suitable for use in the present invention has to be soluble in lipiodol, and preferably is a $C_{12}$–$C_{22}$ unsaturated fatty acid such as linoleic acid. It is desirable that the amount of the $C_{12}$–$C_{22}$ fatty acid contained in the B-lipiodol of the present invention is as low as possible but is sufficient to render all lecithin soluble in the lipiodol. Preferably, the B-lipiodol contains 0.05–0.3 g of the $C_{12}$–$C_{22}$ fatty acid, and more preferably, about 0.2 g of the $C_{12}$–$C_{22}$ fatty acid, per mL lipiodol.

The submicron boron powder used in the present invention have diameters less than 1 $\mu$m, and substantially ranging between 0.1 to 0.9 $\mu$m. The amount of the submicron boron powder which is able to be retained in the B-lipiodol as a dispersion depends on the amount of the lecithin contained therein. That is the lecithin has a boron carrying capacity. On the other hand, the lecithin per se needs the $C_{12}$–$C_{22}$ fatty acid to be soluble in lipiodol as mentioned above. Preferably, the B-lipiodol of the present invention contains 200–3000 ppm of the submicron boron powder, based on the total weight of the B-lipiodol.

DETAILED DESCRIPTION OF THE INVENTION

Figure 1:
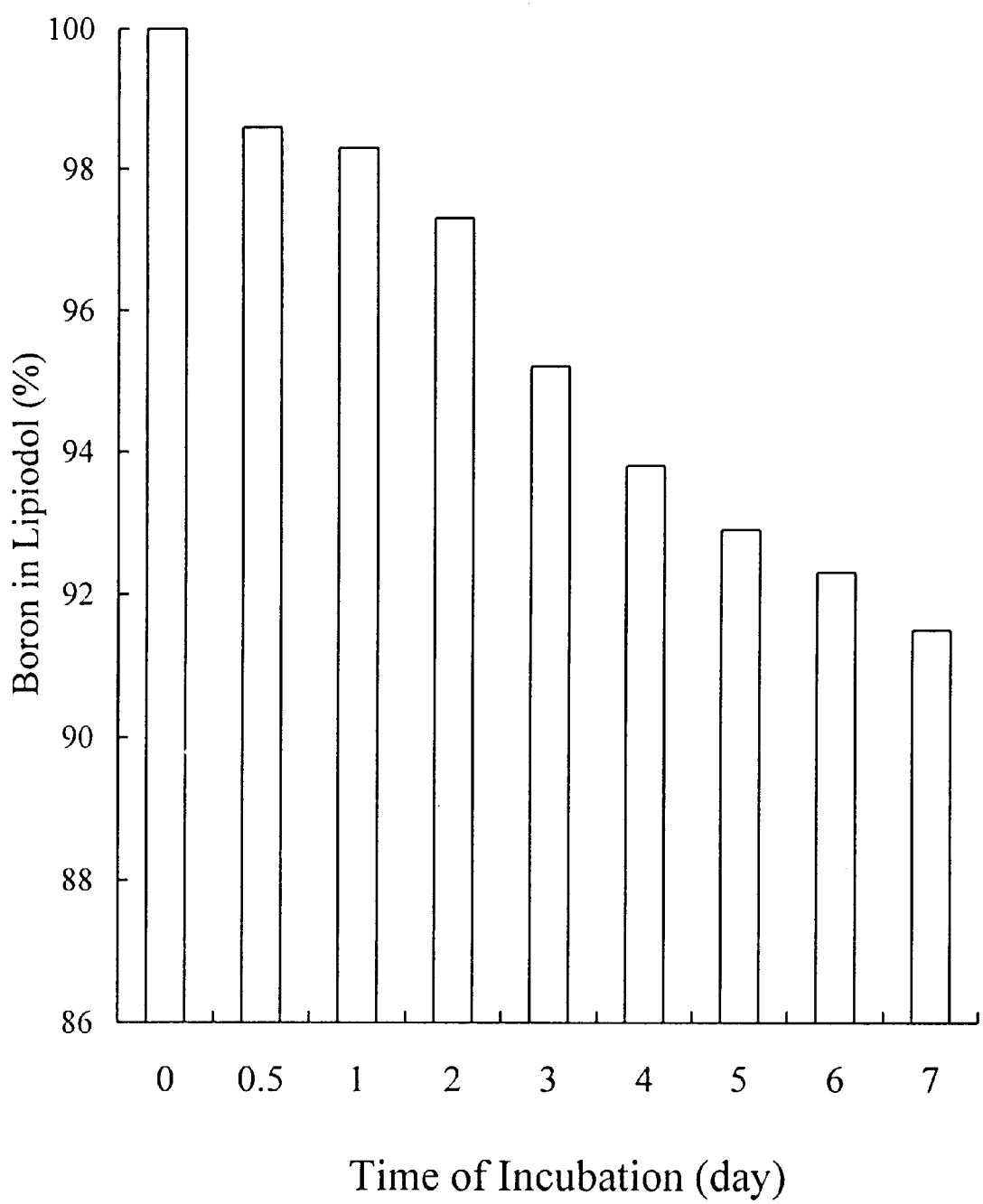
FIG. 1 shows the stability of the B-lipiodol of the present invention in human serum at 37° C., wherein x-axis is the time (day) of incubation of B-lipiodol in human serum, and y-axis is the content (%) of submicron boron powder in the B-lipiodol.

In this invention, I not only prepared the boron-containing lipiodol (B-lipiodol) for boron neutron capture therapy, but also evaluated the cytotoxicity of B-lipiodol on hepatoma cells after neutron irradiation. HepG2 cell culture was used to examine the uptake and retention of B-lipiodol. 1 MWV Tsing Hua Open-pool Reactor (THOR) with a neutron flux of $10^9 n/cm^2$-s was also used for irradiating the B-lipiodol treated HepG2 cells. In addition, the surviving fraction of HepG2 cells was utilized to assess the cytotoxic effect of boron neutron capture.

A suitable process for preparing the B-lipiodol of the present invention comprises the following steps:
 a) mixing the submicron boron powder with an anhydrous inert organic solvent to obtain a homogenous mixture A;
 b) mixing the lipiodol, the $C_{12}$–$C_{22}$ fatty acid and the lecithin with an anhydrous inert organic solvent same as in step a) to form a homogenous mixture B;
 c) adding slowly or in a delayed manner the homogenous mixture A to the homogenous mixture B while stirring to obtain a homogenous mixture C; and
 d) removing the anhydrous inert organic solvent from the homogenous mixture C by evaporation so that an oily suspension liquid containing said submicron boron power is formed;
wherein said anhydrous inert organic solvent is substantially free of water and is not able to chemically react with the submicron boron powder, the lipiodol, the $C_{12}$–$C_{22}$ fatty acid or the lecithin. A suitable example of said anhydrous inert organic solvent is an anhydrous ethanol.

Preferably, in step b) the lipiodol, the $C_{12}$–$C_{22}$ fatty acid and the lecithin are added to the anhydrous inert organic solvent in sequence while stirring.

The process of the present invention may further comprises the following step:
 d) sterilizing the oily suspension liquid from step d), and preferably by Co-60 irradiation.

EXAMPLE

I. Preparation of B-lipiodol Having Different Contents of Submicron Boron Powder In a round flask 0.02 g submicron boron powder (Aldrich Chemical Co., Inc., U.S.; code: 33,244-5) and 16 mL anhydrous ethanol were added and then heated at 70° C. for 10 minutes while stirring, so that a suspension liquid A was obtained. In another round flask 16 mL anhydrous ethanol and 4 mL lipiodol® ultra-fluide (Guerbet Lab., Aulnay-Sous-Bios, France; 38 wt % iodine; 0.48 g iodine/mil) were mixed and then heated at 70° C. for 10 minutes while stirring. To the solution 0.8 mL linoleic acid (Sigma Chemical Co., Code: L-1376, density: 0.9007) was added while maintaining the stirring at 70° C. for another 10 minutes followed by adding 0.6 g lecithin (Sigma Chemical Co., code: P-5394, density: 1.0305) and stirring at 70° C. for another 10 minutes, so that a liquid B was formed. To the liquid B the suspension liquid A was added slowly at 70° C. while stirring, and the resulting mixture after stirring for a period of 10 minutes was placed in a rotary evaporator at 70° C. to remove the ethanol therefrom thoroughly, so that a boron-containing lipiodol (B-lipiodol) was obtained in the form of an oily brown suspension liquid. The B-lipiodol was sterilized by Co-60 irradiation of 1.5 Mrad dose.

The content of the submicron boron powder in the B-lipiodol prepared above was measured by inductively coupled plasma-atomic spectroscopy (ICP-AES) after the B-lipiodol was microwave digested. The result is 3000 ppm based on the total weight of the B-lipiodol.

The above procedures were repeated to prepare B-lipiodol having various contents of the submicron boron powder according to the formulas listed as follows:

| Lipiodol (mL) | Linoleic acid (mL) | Lecithin (g) | Boron powder (g) | Boron content (ppm) |
|---|---|---|---|---|
| 4 | 0 | 0 | 0.02 | 20[a] |
| 4 | 0.4 | 0 | 0.02 | 30[a] |
| 4 | 0 | 0.4 | 0.02 | 400[b] |
| 4 | 0.1 | 0.2 | 0.02 | 1600[c] |
| 4 | 0.2 | 0.1 | 0.02 | 1700 |
| 4 | 0.36 | 0.24 | 0.02 | 2500 |
| 4 | 0.4 | 0.3 | 0.02 | 3000 |
| 4 | 1.2 | 0.9 | 0.02 | 2600[d] |

[a] Most of the submicron boron powder sank to the bottom of the flask and did not suspend in the lipiodol.
[b] Most of the submicron boron powder was in the lecithin which was in the form of gel and not miscible with the lipiodol.
[c] Most of the submicron boron powder was in the lecithin, but 0.1 mL linoleic acid was insufficient to render all lecithin soluble in the lipiodol.
[d] The amounts of linoleic acid and lecithin were too much so that the B-lipiodol was found not stable in serum in the following stability test.

II. The Stability of B-lipiodol

A complete Dulbecco's Modified Eagle Medium (CDMEM) was used in the stability test, which contained 2 mM L-glutamine, 100 IU/mL Penicillium G, 0.1 mg/mL Streptomycin, 0.1 mM non-essential amino acid and 10% heat-inactivated fetal bovine serum, and was adjusted to a pH value of 7.2. B-lipiodol having 3000 ppm submicron boron powder, prepared as described in the section I, appeared as a brown oily agent. Light microscopic examination revealed the presence of brown boron within the droplets of lipiodol contrast medium. 0.15 mL of the B-lipiodol was added to 100 mL of the complete Dulbecco's Modified Eagle Medium (CDMEM), and then homogenized by sonication of 75 W power under sterile condition so that a B-lipiodol-CDMEM liquid was formed. In the B-lipiodol-CDMEM liquid, B-lipiodol vesicles were formed and suspended in the CDMEM. The size of B-lipiodol globules was measured with a photon correlator (LPA-3000), and has a mean diameter of 1.5 $\mu$m which ranges from 0.5 to 5 $\mu$m. After maintaining the B-lipiodol-CDMEM medium at 4° C. for 3 weeks, microscopic observation confirmed that the brown boron still remained in the lipiodol droplets.

For testing the stability of B-lipiodol in human serum, 0.1 ml of B-lipiodol having 3000 ppm submicron boron powder was mixed with 5mL human serum at 37° C., and then sonicated to form a suspension of B-lipiodol vesicles in the serum. For quantitatively testing the release of boron from the oily preparation into the aqueous serum, 1 ml of serum was sampled from each test tube which was maintained at 37° C. and rotated with 75 rpm per day from 1 to 7 days. The boron contents of the samples were measured by ICP-AES, and the results are shown in FIG. 1. According to FIG. 1, most of the boron was stably retained in the oily phase, and 92% of the boron was still retained in the B-lipiodol vesicles after one week.

III. Interaction and Retention of B-lipiodol by HepG2 Cells 7 mL of the B-lipiodol-CDMEM was added to HepG2 cells which were cultured in CDMEM to 70% confluence, and the absolute boron content in the culture after the addition was 8 $\mu$g. The lipiodol-CDMEM and CDMEM supplemented HepG2 cell cultures were used for comparison. When HepG2 cells were incubated with B-lipiodol-CDMEM, the B-lipiodol globules were detected on the cell membrane by inverted light microscopic examination. After 1 h, the B-lipiodol on the cell membrane was found to be emulsified to form smaller lipiodol globules. The smaller B-lipiodol globules were distributed specifically on the surface of HepG2 cells. After 3 h of incubation with B-lipiodol-CMEM, most of the HepG2 cells had intracellular B-lipiodol globules in the cytoplasm, as confirmed by inverted light microscope. At 6 h, the intracellular B-lipiodol globules appeared to be larger in size and quantity. By 48 and 72 h, large numbers of B-lipiodol globules accumulated in the cytoplasm, causing the cell size to enlarge and the plasma membrane to bulge. The lipiodol treated ones yielded the same results. However, none of the above changes occurred in HepG2 cells of the CDMEM control group.

Figure 2:
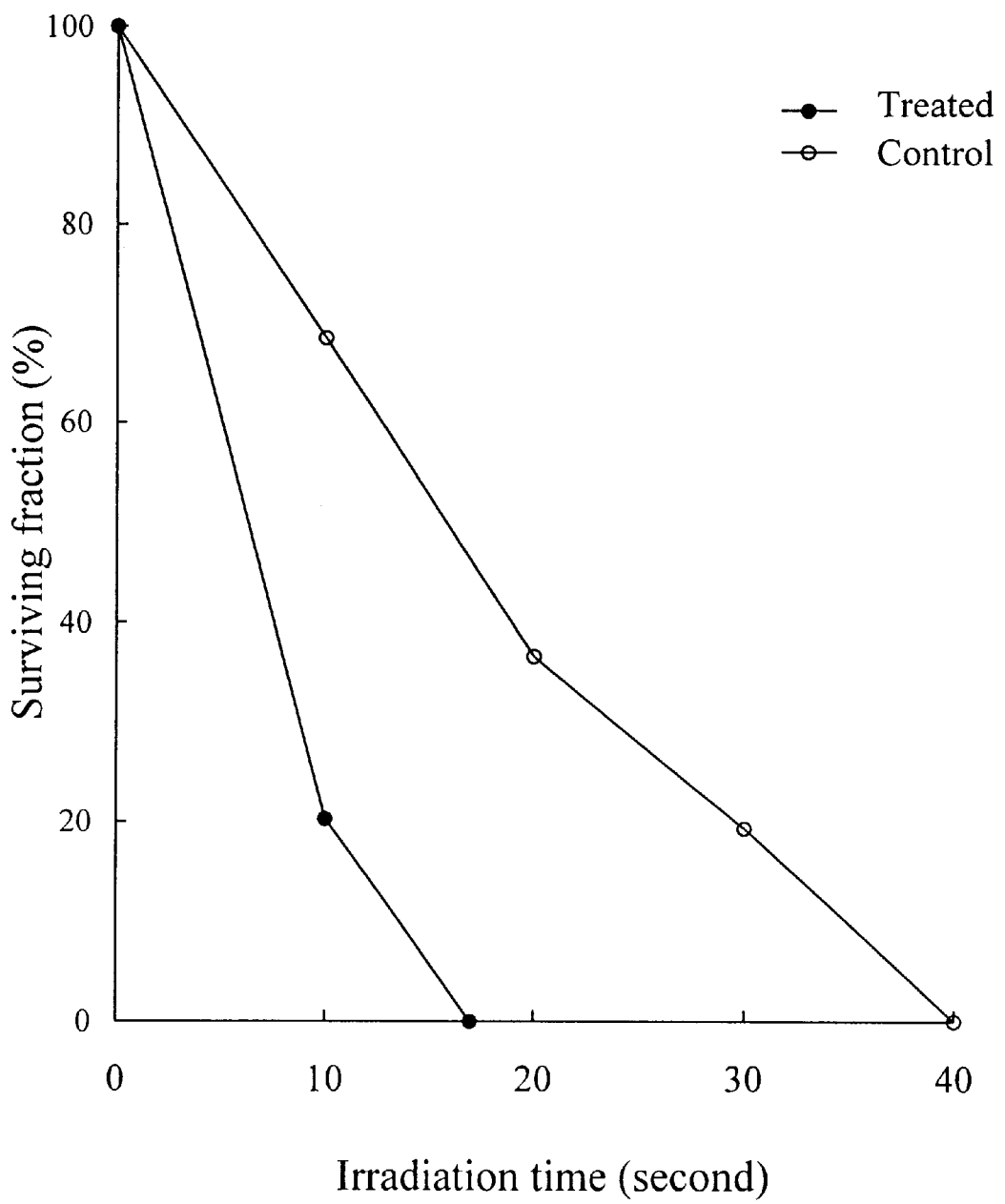
FIG. 2 shows the surviving curves of HepG2 cells treated (black dots) and untreated (by blank circles) by B-lipiodol after neutron capture, wherein x-axis is the irradiation time (second), and y-axis is surviving faction (%).

IV. Cytotoxicity of B-lipiodol on HepG2 Cells After Neutron Irradiation 7 mL of the B-lipiodol-CDMEM was added to HepG2 cells which were cultured in CDMEM to 70% confluence, and the absolute boron content in the culture after the addition was 8 μg. After exposing of the HepG2 cells to B-lipiodol CDMEM for 24 hours, cells were washed twice with 5 ml of phosphate buffer (pH 7.4) to remove any loosely attached B-lipiodol, and then treated with 0.125% (wt/vol) trypsin in 0.05% (wt/vol) EDTA for 5 minutes at 37° C. Cell pellets were washed thoroughly with phosphate buffer by resuspension and centrifugation. About $1 \times 10^6$ HepG2 cell samples in triplicates in polyethylene bags were placed in a cylinder of 50 mm in length, 25 mm in diameter and 0.5 mm in thickness. The cylinder was transferred to a neutron flux of $1 \times 10^9$ n/cm$^2$·s in a vertical tubes of the 1 MW Tsing Hua Open-pool Reactor (THOR) facility. After irradiating, HepG2 cell samples were taken from the cylinder. The viability of B-lipiodol supplemented HepG2 cells after neutron irradiation treatment was determined by the colony forming assay. Changes in cellular morphology were examined by light microscope. HepG2 cells untreated by B-lipiodol were used as control. The results are shown in FIG. 2 and Table 1. It can be seen from FIG. 2 and Table 1 that, after neutron irradiation, the survival curve of HepG2 cells treated by B-lipiodol was more steep than that of the control, and the surviving fraction of the HepG2 cells treated by B-lipiodol reaches 0% after 17-second neutron irradiation. This indicates the B-lipiodol is highly cytotoxic to HepG2 cells after neutron capture.

TABLE 1

| Irradiation time (second) | Surviving fraction (%) | |
|---|---|---|
| | Control | B-lipiodol treated |
| 0 | 100 | 100 |
| 10 | 68.5 | 20.3 |
| 17 | — | 0 |
| 20 | 36.6 | 0 |
| 30 | 19.3 | — |
| 40 | 0 | — |

The B-lipiodol of the Present Invention is Advantageous in:
(1) It can be easily prepared.
(2) It is stable in serum for a substantially long period of time.
(3) It can be selectively accumulated in HepG2 cells with a high concentration, and cytotoxic to HepG2 cells in boron neutron capture therapy.

What is claimed is:

1. A boron-containing pharmaceutical composition for boron neutron capture therapy comprising lipiodol, submicron boron powder, lecithin and $C_2$–$C_{22}$ fatty acid, wherein said submicron boron powder is suspended in said lipiodol in the presence of said lecithin and said $C_{12}$–$C_{22}$ fatty acid.

2. The pharmaceutical composition according to claim 1 comprising 0.01–0.3 g lecithin, and 0.01–0.4 g $C_{12}$–$C_{22}$ fatty acid per mL of lipiodol, and 100–5000 ppm submicron boron powder based on the total weight of the B-lipiodol.

3. The pharmaceutical composition according to claim 2 comprising 0.05–0.2 g lecithin per mL of lipiodol.

4. The pharmaceutical composition according to claim 3 comprising about 0.15 g lecithin per mL of lipiodol.

5. The pharmaceutical composition according to claim 2 comprising 0.05–0.3 g $C_{12}$–$C_{22}$ fatty acid per mL of lipiodol.

6. The pharmaceutical composition according to claim 5 comprising about 0.2 g $C_{12}$–$C_{22}$ fatty acid per mL of lipiodol.

7. The pharmaceutical composition according to claim 2 comprising 200–3000 ppm submicron boron powder based on the total weight of the B-lipiodol.

8. The pharmaceutical composition according to claim 1, wherein said $C_{12}$–$C_{22}$ fatty acid is soluble in said lipiodol.

9. The pharmaceutical composition according to claim 8, wherein said $C_{12}$–$C_{22}$ fatty acid is $C_{12}$–$C_{22}$ unsaturated fatty acid.

10. The pharmaceutical composition according to claim 9, wherein said $C_{12}$–$C_{22}$ unsaturated fatty acid is linoleic acid.

11. The pharmaceutical composition according to claim 1, wherein said submicron boron powder have diameters less than 1 μm, and substantially ranging between 0.1 to 0.9 μm.

12. The pharmaceutical composition according to claim 1, wherein said lipiodol is an iodine addition product of vegetable oils containing 38–42 wt % organically combined iodine.

13. A method for treating hepatoma in a patient comprising administrating a therapeutically effective amount of the pharmaceutical composition of claim 1 to said patient, and subjecting hepatoma with neutron irradiation.

14. The method according to claim 13, wherein said pharmaceutical composition comprises 0.01–0.3 g lecithin, and 0.01–0.4 g $C_{12}$–$C_{22}$ fatty acid per mL of lipiodol, and 100–5000 ppm submicron boron powder based on the total weight of the B-lipiodol.

15. The method according to claim 14, wherein said pharmaceutical composition comprises 0.05–0.2 g lecithin per mL of lipiodol.

16. The method according to claim 15, wherein said pharmaceutical composition comprises about 0.15 g lecithin per mL of lipiodol.

17. The method according to claim 14, wherein said pharmaceutical composition comprises 0.05–0.3 g $C_{12}$–$C_{22}$ fatty acid per mL of lipiodol.

18. The method according to claim 17, wherein said pharmaceutical composition comprises about 0.2 g $C_{12}$–$C_{22}$ fatty acid per mL of lipiodol.

19. The method according to claim 14, wherein said pharmaceutical composition comprises 200–3000 ppm submicron boron powder based on the total weight of the B-lipiodol.

20. The method according to claim 13, wherein said $C_{12}$–$C_{22}$ fatty acid is soluble in said lipiodol.

21. The method according to claim 20, wherein said $C_{12}$–$C_{22}$ fatty acid is $C_{12}$–$C_{22}$ unsaturated fatty acid.

22. The method according to claim 21, wherein said $C_{12}$–$C_{22}$ unsaturated fatty acid is linoleic acid.

23. The method according to claim 13, wherein said submicron boron powder have diameters less than 1 μm, and substantially ranging between 0.1 to 0.9 μm.

24. The method according to claim 13, wherein said lipiodol is an iodine addition product of vegetable oils containing 38–42 wt % organically combined iodine.

25. A process for preparing the boron-containing pharmaceutical composition of claim 1, the method comprising:
   a) mixing the submicron boron powder with an anhydrous inert organic solvent to obtain a homogenous mixture A;
   b) mixing the lipiodol, the $C_{12}$–$C_{22}$ fatty acid, and the lecithin with the same anhydrous inert organic solvent as in step to form a homogenous mixture B;
   c) adding the homogenous mixture A slowly or in a delayed manner to the homogenous mixture B while stirring to obtain a homogenous mixture C; and
   d) removing the anhydrous inert organic solvent from the homogenous mixture C by evaporation.

26. The process according to claim 25, wherein said anhydrous inert organic solvent is ethanol.

27. The process according to claim 25, wherein in step b) the lipiodol, the $C_{12}$–$C_{22}$ fatty acid and the lecithin are added to the anhydrous inert organic solvent in sequence while stirring.

28. The process according to claim 25 further comprises the following step:
   e) sterilizing the resulting mixture from step d).

29. The process according to claim 28 wherein said sterilization is carried out by Co-60 irradiation.

\* \* \* \* \*